United States Patent [19]

Yoneyama et al.

[11] 4,095,982
[45] Jun. 20, 1978

[54] METHOD OF DEVELOPING A SILVER HALIDE PHOTOGRAPHIC LIGHT-SENSITIVE MATERIAL

[75] Inventors: Masakazu Yoneyama; Isao Shimamura, both of Minami-ashigara; Shinzo Kishimoto; Kazunori Hasebe, both of Fujimiya, all of Japan

[73] Assignee: Fuji Photo Film Co., Ltd., Minami-ashigara, Japan

[21] Appl. No.: 733,827

[22] Filed: Oct. 19, 1976

[30] Foreign Application Priority Data

Oct. 24, 1975 Japan ................... 50-127989

[51] Int. Cl.² ............... G03C 5/26; G03C 5/30; G03C 1/06
[52] U.S. Cl. ............... 96/50 PT; 96/66 R; 96/66.3; 96/95; 96/107; 96/109
[58] Field of Search ............ 96/66.3, 66 R, 109, 96/107, 114, 95, 50 R, 50 PT

[56] References Cited

U.S. PATENT DOCUMENTS

| 3,671,255 | 6/1972 | Haga | 96/109 |
| 3,827,886 | 8/1974 | Ishihra et al. | 96/109 |

FOREIGN PATENT DOCUMENTS

| 1,937,049 | 2/1970 | Germany | 96/66 R |
| 664,550 | 4/1950 | United Kingdom | 96/109 |
| 667,199 | 2/1952 | United Kingdom | 96/109 |
| 677,264 | 8/1952 | United Kingdom | 96/114 |

*Primary Examiner*—Mary F. Kelley
*Attorney, Agent, or Firm*—Sughrue, Rothwell, Mion, Zinn and Macpeak

[57] ABSTRACT

A development method which comprises developing a silver halide photographic ligh-sensitive material in the presence of a compound represented by the following general formula:

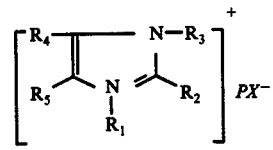

wherein $R_1$, $R_2$, $R_3$, $R_4$ and $R_5$ each represent a hydrogen atom, alklyl group, alkenyl group, aralkyl group or aryl group, X represents an anion, and P is 1 or 2.

22 Claims, No Drawings

METHOD OF DEVELOPING A SILVER HALIDE PHOTOGRAPHIC LIGHT-SENSITIVE MATERIAL

BACKGROUND OF THE INVENTION

1. Field of the Invention

This invention relates to a silver halide photographic light-sensitive material, more particularly, to a method of developing a silver halide photographic light-sensitive material.

2. Description of the Prior Art

For the development of silver halide photographic light-sensitive materials, accelerating of the rate of development and increasing the effective sensitivity of the developed light-sensitive material are desired. For these purposes, it has been known so far to add amine compounds as development accelerators. These amine compounds which are well known include alkylamines (U.S. Pat. No. 2,196,037), aralkylamines (U.S. Pat. Nos. 2,496,903, 2,515,147 and 2,541,889), phenoxyalkylamines (U.S. Pat. No. 2,482,546), heterocyclic alkylamines (U.S. Pat. No. 2,605,183), morpholine, piperidine, etc. (U.S. Pat. No. 2,304,025), xylylenediamines (British Pat. No. 1,086,618), and the like.

However, these amines, in general, are bad-smelling and volatile, and therefore, it is difficult to keep their concentrations constant in a processing solution, and they are difficult to handle. Moreover, although they accelerate development when added to a developer, their effect of increasing effective sensitivity is low, and increased fog and a deterioration in the granularity of the developed silver are observed.

In addition, heterocyclic amines in which the above defects are overcome have been patented (U.S. Pat. No. 3,808,003). However, their effect of accelerating development is still insufficient for the object of this invention.

SUMMARY OF THE INVENTION

The object of this invention is to provide a development method which uses a development accelerator which is easy to handle, accelerates the rate of development, increases effective sensitivity causes no increase in fog and no deterioration in the granularity of developed silver.

This invention provides a method of processing a silver halide photographic light-sensitive material which comprises developing the photographic light-sensitive material in the presence of an imidazolium salt derivative represented by the following general formula (I):

General Formula (I)

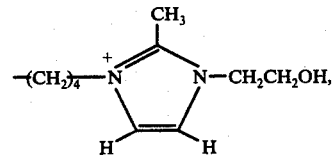

wherein $R_1$, $R_2$, $R_3$, $R_4$ and $R_5$ each represents a hydrogen atom, an alkyl group, an alkenyl group, an aralkyl group or an aryl group, P is 1 or 2 and X is an anion.

DETAILED DESCRIPTION OF THE INVENTION

Preferred alkyl groups have up to 18 carbon atoms and may or may not be branched. Preferred alkenyl groups have up to 18 carbon atoms, preferred aralkyl groups have up to 14 carbon atoms, and preferred aryl groups have up to 12 carbon atoms. The alkyl groups may be substituted with, e.g., —CN, —NH₂, —OH, etc. The substituted alkyl groups may be those represented by the following general formula (II):

General Formula (II)

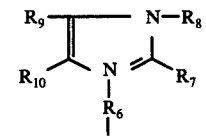

In this formula, $R_6$ represents alkylene having up to 14 carbon atoms, and $R_7$, $R_8$, $R_9$ and $R_{10}$ each represents a hydrogen atom or alkyl, alkenyl, aralkyl or aryl each having up to 14 carbon atoms.

$X^-$ represents an anion containing a monovalent anionic atom or a group which forms a compound such as a halide, alkyl sulfate, alkane sulfonate or aromatic sulfonic acid. Preferred alkyl groups have 1 to 3 carbon atoms, preferred alkane groups have 1 to 3 carbon atoms and preferred aromatic groups have 6 to 9 carbon atoms. The monovalent anionic atom or group serves to render the compounds of the present invention water soluble, as is well known in the art, and so long as this criterion is met, such groups can be freely selected.

Specific examples of $R_1$, $R_2$, $R_3$, $R_4$ and $R_5$ are alkyl groups such as methyl, ethyl, propyl, (n- and iso), hexyl, octyl, decyl, dodecyl, tetradecyl, hexadecyl and octadecyl, alkenyl groups such as vinyl and allyl, oleyl, hydroxyethyl, cyanoethyl, aminopropyl and

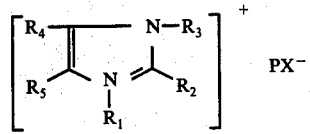

aralkyl such as benzyl, phenethyl, etc., aryl such as phenyl, naphthyl, etc. Specific Examples of X are Cl, Br and I.

Some specific examples of the compounds used in this invention are given below.

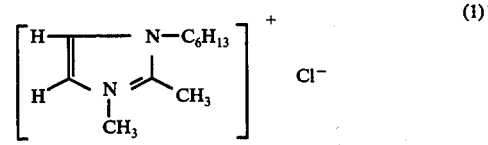

(1)

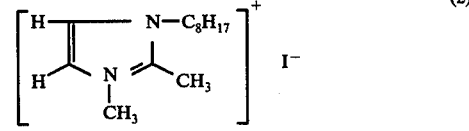

(2)

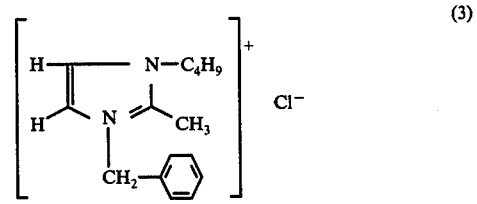

(3)

-continued (4) 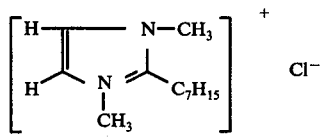

(5) 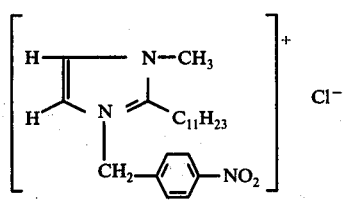

(6) 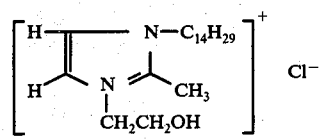

(7) 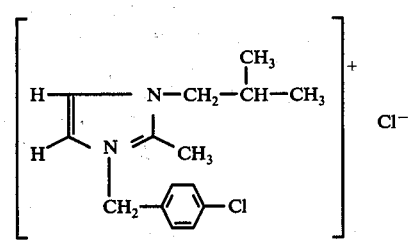

(8) 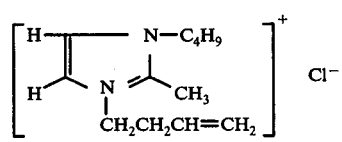

(9) 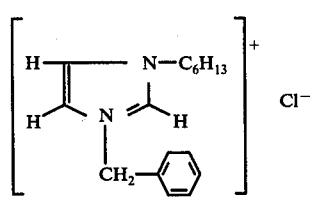

(10) 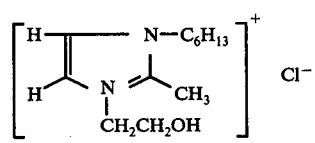

(11) 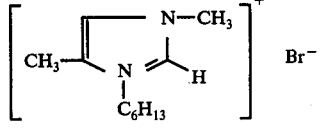

(12) 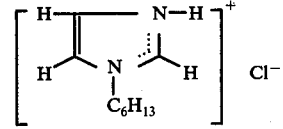

-continued

(13) 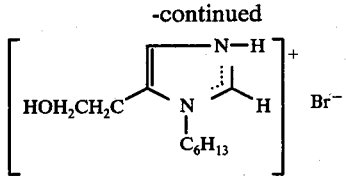

(14) 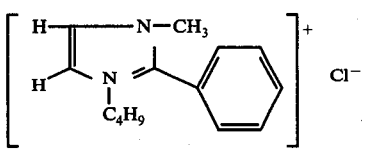

(15) 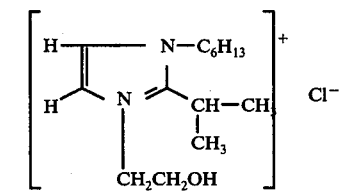

(16) 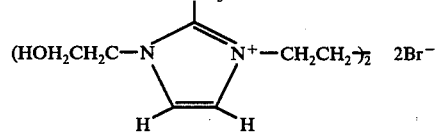

(17) 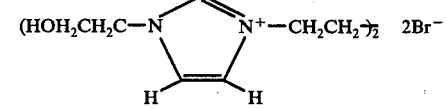

These compounds can be synthesized by processes as described in the following literature: A. A. Morton, *The Chemistry of Heterocyclic Compound*, (1949); Elderfield, *Heterocyclic Compounds*, Vol.1, p.5, Wiley Inc. (1957); K. Hofman, *Imidazole and its Derivatives*, Part 1, Interscience Inc.; (1953); A. R. Katritzky, *Advances in Heterocyclic Chemistry*, Vol.3, p.17 (1964), Vol.7, p.251 (1966), Vol.12, p.104 (1970), Academic Press; Japanese Patent Publications Nos. 13,872/65, 4,153/67 and 12,354/68.

This invention is applicable to conventional silver halide light-sensitive materials, for example, conventional black-and-white light-sensitive materials, light-sensitive materials for printing, color light-sensitive materials, etc. In particular, this invention is effective to accelerate development of silver iodobiomide emulsions containing not less than 2 mol% of silver iodide.

Highly preferred materials are color X-ray photographic materials as disclosed in U.S. Pat. Nos. 3,622,629 and 3,627,530.

In particular, when the compound of this invention is used, no deterioration of granularity and no occurrence of fog is caused even in rapid processing in which the temperature of development is raised. Therefore, this invention is particularly advantageously applied for color radiation-sensitive materials for radiography for which rapid processing is required.

Color radiation-sensitive materials for radiography have long been known and are roughly classified into:(A) those of the type forming a color image using conventional multilayer color light-sensitive materials as such and subjecting the same to a conventional color development, as described in U.S. Pat. Nos. 2,807,725, 2,931,904 and 3,114,833; (B) those of the type forming a color image by subjecting coupler-containing light-sensitive matetrials to a conventional color development, as described in U.S. Pat. Nos. 2,994,610 and 3,121,232, and French Pat. No. 2,077,659; and (C) those of the type forming an image comprising a dye and silver by subjecting a coupler-containing light-sensitive material to conventional color development - fixing - washing steps (not including a bleaching step), as described in U.S. Pat. Nos. 3,622,629; 3,627,530; 3,734,735 and 3,809,906, British Pat. Nos. 112,085, German Patent Laid-Open Application (OLS) No. 1,158,836, and Japanese Patent Application (OPI) No. 37,539/72.

Color radiation-sensitive materials have many advantages such as high distinguishability, large exposure latitude, can record high amounts of information due to their good granularity, as well as the fact that a small amount of silver halide is contained therein and they have low cost, as compared with black-and-white radiation-sensitive materials for radiography.

For radiation-sensitive materials, extremely rapid processings are desired from the viewpoint of use, and for the black-and-white radiation-sensitive materials, processes in which all of the steps of development - fixing - washing - drying are effected within 2 minutes are usually employed.

Similarily to black-and-white radiation-sensitive materials, rapid processing is, of course, required for the color radiation-sensitive materials. Among the aforesaid types (A), (B) and (C), light-sensitive materials of type (C), the processing of which includes no bleaching step, are most practical from the viewpoint of rapid processing. Moreover, light-sensitive materials of type (C) can provide a high image density even if the amount of silver halide present is small, since color images and silver images are present together, and they contribute together, and they contribute to image density. Therefore, particularly preferred color radiation-sensitive materials are those of type (C).

However, color development for the light-sensitive materials of type (C) is the same as a conventional color development in that coupler-containing light-sensitive materials are subjected to color development using an aromatic primary amine developing agent, and, therefore, it has the disadvantage that development accelerating effects are poor as compared with conventional black-and-white development.

Therefore, the technique of accelerating development in the color development of color radiation-sensitive materials without causing problems such as increased fog and deterioration of granularity is highly desired, and the development method of this invention is particularly suitable for this purpose.

The compounds of this invention are superior in both their development accelerating effect and their sensitizing effect to thiocyanic acid salts, alkylamines, and the like, which are usually employed. Moreover, the image quality of the photographic image obtained is superior in shapness.

In addition, in usual light-sensitive materials for photography, the compounds of this invention can accelerate development and increase sensitivity while causing less increased fog.

Also, in lith type development, development acceleration can be obtained without lowering the dot efficiency.

Since the compounds of this invention have such an excellent development accelerating effect, the addition of the compounds of this invention enables development acceleration and also permits rapid processing without raising the temperature of development. Further, rapid processing can be effected, of course, by raising the temperature of development and adding the compounds of this invention.

Amine compounds are bad-smelling and volatile, and, therefore, it is difficult to keep their concentrations constant in the processing solution, and they cannot be easily handled because of their toxicity. Moreover, their effects of accelerating development and of increasing sensitivity are low, and they are further disadvantageous in that undesirable phenomena occur such as increased fog, the occurrence of scum and a deterioration of the granularity of the developed silver. However, the compounds of this invention are quite free from these defects.

The developers to which compounds of this invention can be added to accelerate development are those usually used in silver halide photography, i.e., there is no limitation on the developer selected, and the developer is typically an aqueous solution containing one or more developing agents, e.g., dihydroxybenzene derivatives such as hydroquinone or catechol; ascorbic acid derivatives, e.g., l-ascorbic acid or d-araboascorbic acid; 3-pyrazolidone derivatives such as 1-phenyl-3-pyrazolidone or 4,4-dimethyl-1-phenyl-3-pyrazolidone; aminophenol derivatives such as N-methyl-p-aminophenol or N,N-diethyl-p-aminophenol; p-phenylenediamine derivatives such as N,N-diethyl-p-phenylenediamine, N-ethyl-N-hydroxyethyl-p-phenylenediamine, 2-amino-5-diethylaminotoluene or N,N,N',N'-tetramethyl-p-phenylenediamine; etc.

Moreover, an antioxidant such as sodium sulfite or ascorbic acid, a salt such as sodium sulfate, a pH modifier or a buffer such as boric acid, borax, sodium hydroxide, sodium carbonate or sodium tertiary phosphate, a development inhibitor such as potassium bromide or potassium iodide, an organic antifogging agent such as 6-nitrobenzimidazole or benzotriazole, and the like can be added. In addition, aldehydes such as formalin or glutaraldehyde may be added.

The amount of the one or more developing agents utilized is not especially limited and can be freely selected from those amounts used in the art; typically, the amount is on the order of about 1 to about 200 g/l.

The developer is typically utilized at an alkaline pH, e.g., at a pH of 9 to 12, though this is not limitative.

The compounds of this invention are effective in any case where they are added to a developer, to a silver halide emulsion or to a prebath before development, but higher effects are obtained by addition to the developer. If added to a prebath, typically this will comprise an aqueous solution of the compound, and the amount of the compound (or compounds) will be on the order of about 1 to about 10 g/l of prebath.

In adding to the developer, the compound of this invention is usually employed in an amount ranging from about 0.01 g to about 100 g per 1 liter of the developer, although the amount depends upon the composition of the developer. The most effective amount thereof is about 0.05 g to about 10 g.

In adding the compound to a silver halide emulsion, a suitable addition amount is about 0.01 g to about 50 g per 1 mol of silver halide. The addition of the compound of this invention to the silver halide emulsion may be effected in any step of the production of the emulsion, but it is particularly effective to add it after second ripening but before coating. Instead of direct addition to the emulsion layer, the compound of this invention may be added to an adjacent layer, such as a protective layer, and permeated into the emulsion layer. In the case of addition to an adjacent layer, the amount is the same as in the case of addition to a silver halide emulsion.

As should be apparent to one skilled in the art, if desired, mixtures of more than one compound in accordance with the present invention can be utilized, and, further, if desired, the compound or compounds utilized can be present in both a processing bath and the element, if desired.

In the photographic light-sensitive material of this invention, there can be used all supports which are generally used for photographic light-sensitive materials. Examples thereof are cellulose nitrate films, cellulose acetate films, cellulose acetate butyrate films, cellulose acetate propionate films, polystyrene films, polyethylene terephthalate films, polycarbonate films, laminates thereof, and papers, and these supports may be colored. Dyes for coloring the films are described, e.g., in U.S. Pat. Nos. 2,571,319; 3,372,138; 3,488,195; 3,359,230; 3,413,257; 3,530,132 and 3,487,041. Moreover, papers coated or laminated with baryta or an α-olefin polymer, particularly a polymer of an α-olefin having 2 to 10 carbon atoms, such as polyethylene or polypropylene, and plastic films the surface of which is matted to improve the adhesion with other high molecular weight substances and improve printability as described in Japanese Patent Publication No. 19,068/72 are preferred supports.

In the photographic light-sensitive material of this invention, various hydrophilic colloids are used, and examples of the hydrophilic colloids which are used as binders for photographic emulsions and/or other photographic layers include gelatin, colloidal albumin, casein, cellulose derivatives such as carboxymethyl cellulose or hydroxyethyl cellulose, saccharides such as agar or sodium alignate and synthetic hydrophilic colloids such as polyvinyl alcohol, poly-N-vinyl pyrrolidone, polyacrylic acid copolymers, polyacrylamide or derivatives thereof or partially hydrolyzed products thereof. If desired or necessary, a compatible mixture of two or moreof these colloids can be used.

Among the above colloids, gelatin is most generally used, but gelatin can be, partially or completely, replaced with a synthetic high molecular weight substance. Furthermore, gelatin can be replaced with a gelatin derivative, i.e., one prepared by treating and modifying the functional groups contained in the gelatin molecule (such as an amino group, imino group, hydroxy group or carboxyl group) with a reagent having a group capable of reacting with such a functional group, or a graft polymer prepared by grafting the molecular chain of another high molecular weight substance into gelatin.

The photographic emulsion layer and other layers used in this invention may contain a synthetic polymer compound such as a latex of a water-dispersible vinyl compound polymer, particularly a compound capable of increasing the dimensional stability of photographic materials, alone or as a mixture (of the different polymers) or in combination with a hydrophilic water-permeable colloid. A number of such polymers are known and described, e.g., in U.s. Pat. Nos. 2,376,005; 2,739,137; 2,853,457; 3,062,674; 3,411,911; 3,488,708; 3,525,620; 3,635,715; 3,607,290 and 3,645,740; British Pat. Nos. 1,186,699 and 1,307,373, etc. Of these polymers, copolymers or homopolymers of alkyl acrylates, alkyl methacrylates, acrylic acid, methacrylic acid, sulfoalkyl acrylates, sulfoalkyl methacrylates, glycidyl acrylate, glycidyl methacrylate, hydroxyalkyl acrylates, hydroxyalkyl methacryaltes, alkoxyalkyl acrylates, alkoxy methacrylates, styrene, butadiene, vinyl chloride, vinylidene chloride, maleic anhydride and itaconic anhydride are generally used. If desired, a graft emulsionpolymerized latex which is prepared by subjecting the vinyl compounds to emulsion polymerization in the presence of a hydrophilic protective colloid high molecular weight substance can be used.

The hardening of the photographic emulsion and/or other photographic layers can be effected in a conventional manner, if desired. Specific examples of hardners are aldehyde compounds such as formaldehyde or glutaraldehyde; ketones such as diacetyl or cyclopentanedione; compounds having a reactive halogen such as bis-(2-chloroethylurea), 2-hydroxy-4,6-dichloro-1,3,5-triazine and compounds as described in U.S. Pat. Nos. 3,288,775 and 2,732,303, and British Pat. Nos. 974,723 and 1,167,207; compounds having a reactive olefin bond such as divinyl sulfone, 5-acetyl-1,3-diacryloylhexahydro-1,3,5-triazine and compounds as described in U.S. Pat. Nos. 3,635,718, 3,232,763, 3,490,911 and 3,642,486, and British Pat. No. 994,869; N-methylol compounds such as N-hydroxymethylphthalimide and compounds as described in U.S. Pat. Nos. 2,732,316 and 2,586,168; isocyanates as described in U.S. Pat. No. 3,103,437; aziridine compounds as described in U.S. Pat. Nos. 3,017,280 and 2,983,611; acid derivatives as described in U.S. Pat. Nos. 2,725,294 and 2,725,295; carbodiimide compounds as described in U.S. Pat. No. 3,100,704; epoxy compounds as described in U.S. Pat. No. 3,091,537; isoxazole compounds as described in U.S. Pat. Nos. 3,321,313 and 3,543,292; halogenocarboxyaldehydes such as mucochloric acid; dioxane derivatives such as dihydroxydioxane and dichlorodioxane; and inorganic hardeners such as chrome alum and zirconium sulfate. In place of the above compounds, those in the form of a precursor thereof such as alkali metal bisulfite aldehyde adducts, methylol derivatives of hydantoin and primary aliphatic nitroalcohols can also be used.

The silver halide photographic emulsion is usually prepared by mixing a solution of a water-soluble silver salt (such as silver nitrate) with a solution of a water-soluble halogen salt (such as potassium bromide) in the presence of a solution of a water-soluble high molecular weight substance such as gelatin.

Silver halides which can be used include silver chloride and silver bromide, as well as mixed silver halides such as silver chlorobromide, silver bromoiodide and silver chlorobromoiodide. For the color radiation-sensitive materials, silver bromoiodide containing not more than 10 mol % silver iodide is preferred.

These silver halide grains can be prepared in known conventional manners. It is also advantageous, of course, to prepare the grains by a single or double jet method, a controlled double jet method, and the like. Moreover, two or more types of silver halide photographic emulsions separately prepared may be mixed.

Various compounds can be added to the above photographic emulsion in order to prevent a decrease in sensitivity and the occurrence of fog in the production of the light-sensitive material, during the storage thereof or in the course of processing. A large member of such compounds have long been known, for example, 4-hydroxy-6-methyl-1,3,3a,7-tetrazaindene, 3-methylbenzothiazole and 1-phenyl-5-mercaptotetrazole, as well as many heterocyclic compounds, mercury-containing compounds, mercapto compounds, metal salts, etc. Many such compounds which can be used are described, e.g., in U.S. Pat. Nos. 1,758,576; 2,110,178; 2,131,038; 2,173,628; 2,697,040; 2,304,962; 2,324,123; 2,394,198; 2,444,605 to 8; 2,566,245; 2,694,716; 2,697,099; 2,708,162; 2,728,663 to 5; 2,476,536; 2,824,001; 2,843,491; 2,886,437; 3,052,544, 3,137,577; 3,220,839; 3,226,231; 3,236,652; 3,251,691; 3,252,799; 3,287,135; 3,326,681; 3,420,668; 3,619,198; 3,622,339 and 3,650,759, British Pat. Nos. 893,428; 403,789; 1,173,609 and 1,200,188, etc.

The silver halide emulsion can be chemically sensitized in a conventional manner, if desired. Chemical sensitizers include, for example, gold compounds such as chloroauric salts and auric trichloride as described in U.S. Pat. Nos. 2,399,083; 2,540,085; 2,597,856 and 2,597,915; salts of noble metals such as platinum, palladium, iridium, rhodium and ruthenium as described in U.S. Pat. Nos. 2,448,060; 2,540,086; 2,566, 245; 2,566,263 and 2,598,079; sulfur compounds capable of forming silver sulfide by reacting with a silver salt as described in U.S. Pat. Nos. 1,574,944; 2,410,689; 3,189,458 and 3,501,313; stannous salts as described in U.S. Pat. Nos. 2,487,850; 2,518,698; 2,521,925; 2,521,926; 2,694,637; 2,983,610; and 3,201,254; amines; other reducing compounds, and the like.

In addition, as a development accelerator, quaternary ammonium salts or polyethylene glycols can be added.

The photographic emulsion can be, if desired, spectrally sensitized or supersensitized by using cyanine dyes such as cyanine, merocyanine or carbocyanine dyes, alone or in admixture, or in combination with, e.g., styryl dyes. Such color sensitization techniques have long been known and are described, e.g., in U.S. Pat. Nos. 2,493,748; 2,519,001; 2,977,229; 3,480,434; 3,672,897; 3,703,377; 2,688,545; 2,912,329; 3,397,060; 3,615,635 and 3,628,964, British Pat. Nos. 1,195,302; 1,242,588 and 1,293,862, German Patent Applications Laid-Open (OLS) Nos. 2,030,326 and 2,121,780, Japanese Patent Publications Nos. 4,936/68; 14,030/69 and 10,773/68, U.S. Pat. Nos. 3,511,664; 3,522,052; 3,527,641; 3,615,613; 3,615,632; 3,617,295; 3,635,721 and 3,694,217, British Pat. Nos. 1,137,580 and 1,216,203, etc. The techniques can be optionally selected depending upon the purpose and the use of the light-sensitive material, that is, the wavelength region to be sensitized, sensitivity, and the like.

For example, regular or orthochromatic color sensitivity is conventional for color radiation-sensitive materials, but in spectrally sensitizing color radiation-sensitive materials to the wavelength region of 480 to 600 mμ, sensitizing dyes as described in Japanese Patent Publication No. 14,030/69 and Japanese Patent Applications (OPI) Nos. 33,626/72 and 59,828/73 are preferably used.

The photographic layers of the photographic light-sensitive material of this invention can contain, as a plasticizer, polyols of the type as described in U.S. Pat. Nos. 2,960,404; 3,042,524; 3,520,694; 3,656,956 and 3,640,721.

The photographic light-sensitive material of this invention can contain, in addition to the silver halide emulsion layer, conventional non-light-sensitive photographic layers such as a protective layer, a filter layer, an intermediate layer, an antihalation layer, a subbing layer, backing layer, an antistatic layer and a curl balancing layer. The color radiation-sensitive materials can contain silver halide emulsion layers on both sides of the support as in black-and-white radiation-sensitive materials, if desired.

The non-light-sensitive photographic layers of the photographic light-sensitive material of this invention can contain a brightener such as stilbene, triazine, oxazole or coumarin compounds; an ultraviolet absorbant such as benzotriazole, thiazolidine or cinnamic ester compounds; a light asborbant such as known various photographic filter dyes or dyes for lowering sensitivity to dark room light (a safelight); and a slip agent or an anti-adhesion agent such as water-insoluble substances as described in British Pat. Nos. 1,320,564, and U.S. Pat. No. 3,121,060 or surface active agents as described in U.S. Pat. No. 3,617,286. Moreover, as a matting agent, silver halide having an appropriate particle size, inorganic compounds such as silica or strontium barium sulfate, or a polymer latex such as polymethyl methacrylate can be incorporated therein.

Into the photographic layers, including photographic emulsion layers, of the photographic light-sensitive material of this invention, particularly into an antistatic layer provided as the uppermost layer of the photographic light-sensitive material, there can be incorporated an antistatic agent such as hydrophilic polymers as described in U.S. Pat. Nos. 2,725,297; 2,972,535; 2,972,536; 2,972,537; 2,972,538; 3,033,679; 3,072,484; 3,262,807; 3,525,621; 3,615,531; 3,630,743; 3,653,906; 3,655,384 and 3,655,386, and British Pat. Nos. 1,222,154 and 1,235,075; hydrophobic polymers as described in U.S. Pat. Nos. 2,973,263 and 2,976,148; biguanide compounds as described in U.S. Pat. Nos. 2,584,362 and 2,591,590; sulfonic acid type anionic compounds as described in U.S. Pat. Nos. 2,639,234; 2,649,372; 3,201,251 and 3,457,076; phosphoric esters and quaternary ammonium salts as described in U.S. Pat. Nos. 3,317,344 and 3,514,291; cationic compounds as described in U.S. Pat. Nos. 2,882,157; 2,982,651; 3,399,995; 3,549,369 and 3,564,043; nonionic compounds as described in U.S. Pat. No. 3,625,695; amphoteric compounds as described in U.S. Pat. No. 3,736,268; complex compounds as described in U.S. Pat. No. 2,647,836; and organic salts as described in U.S. Pat. Nos. 2,717,834 and 3,655,387.

This invention is applicable to all types of photographic light-sensitive materials whether they are black-and-white light-sensitive materials or color light-sensitive materials.

The silver halide emulsions of this invention include various silver halide photographic emulsions, e.g., orthochromatic emulsions, panchromatic emulsions, infared photographic emulsions, emulsions for recording invisible rays such as X-rays, color photographic emulsions such as emulsions containing color-forming couplers, emulsions containing a dye developing agent or emulsions containing dyes capable of being bleached, etc.

When the silver halide photographic emulsion of this invention is used for a color phographic light-sensitive material, a compound which can form a dye by reacting with an oxidized developing agent, i.e., a coupler, is incorporated into the light-sensitive photographic emulsion layer. The couplers have such a structure that they do not diffuse to other layers during production or processing.

As yellow-forming couplers, open-chain diketomethylene compounds are generally used widely. Examples of them are described in U.S. Pat. Nos. 3,341,331; 2,875,057 and 3,551,155, German Patent Application Laid-Open (OLS) No. 1,547,868, U.S. Pat. Nos. 3,265,506; 3,582,322 and 3,725,072, German Patent Application Laid-Open (OLS) No. 2,162,899, U.S. Pat. Nos. 3,369,895 and 3,408,194, and German Patent Applications Laid-Open (OLS) Nos. 2,057,941; 2,213,461; 2,219,917; 2,261,361 and 2,263,875.

As magenta couplers, 5-pyrazolone compounds are mainly used, but indazolone compounds and cyanoacetyl compounds are also used. They are described, e.g., in U.S. Pat. Nos. 2,439,098; 2,600,788; 3,062,653 and 3,558,319, British Pat. No. 956,261, U.S. Pat. Nos. 3,582,322; 3,615,506; 3,519,429; 3,311,476 and 3,419,391; Japanese Patent Applications Nos. 21,454/73 and 56,050/73; German Pat. No. 1,810,464; Japanese Patent Publication No. 2,016/69, Japanese Patent Application No. 45,971/73, U.S. Pat. No. 2,983,608, etc.

As cyan couplers, phenol or naphthol derivatives are mainly used. They are described, e.g., in U.S. Pat. Nos. 2,369,929; 2,474,293; 2,698,794; 2,895,826; 3,311,476; 3,458,315; 3,560,212; 3,582,322; 3,591,383; 3,386,301; 2,434,272; 2,706,684; 3,034,892 and 3,583,971; German Patent Application Laid-Open (OLS) No. 2,163,811, Japanese Patent Publication No. 28,836/70, Japanese Patent Application No. 33,238/73, etc.

In addition, a coupler which releases, on color formation reaction, a compound having a development inhibiting effect ( a DIR coupler ) and a compound which releases a compound having a development inhibiting effect can be added. They are described, e.g., in U.S. Pat. Nos, 3,148,062; 3,227,554; 3,253,924; 3,617,291; 3,622,328 and 3,705,201; British Pat. No. 1,201,110; U.S. Pat. Nos. 3,297,445; 3,379,529 and 3,639,417, etc.

In order to satisfy the characteristics required for the light-sensitive material, the above couplers and the like may be added as a combination of two or more thereof to the same layer, or the compound(s) may, of course, be added to two or more different layers.

As for the color radiation-sensitive materials, there are no particular restrictions on the absorption wavelength region of the color image obtained. However, cyan color images or blue color images having a main absorption in the red wavelength region (600 to 700 m$\mu$) or the longer wavelength region (550 to 600 m$\mu$) of the green wavelength region of the visible spectrum are particularly preferred.

For this purpose, phenolic or $\alpha$-naphtholic colored couplers which form quinoneimine dyes having an absorption maximum in the wavelength region ranging from 550 m$\mu$ to 700 m$\mu$ are particularly preferred.

The couplers which can be used for this purpose are described, e.g., in U.S. Pat. Nos. 2,772,162; 3,222,176; 3,758,308; 3,737,318; 3,591,383 and 3,476,563; British Pat. Nos. 1,201,110; 1,038,331; 727,693 and 747,628; Japanese Patent Application Laid-Open (OPI) No. 4,480/72, etc.

Photographic colored couplers are dispersed by an oil-soluble type dispersing method or a water-soluble type dispersing method.

Preferred couplers for color radiation-sensitive materials are those having hydropilic groups such as a carboxyl group and a sulfo group from the viewpoint of suitability for rapid processing, and for dispersion thereof, the water-soluble type dispersing manner is preferably adopted.

In the oil-soluble type dispersing method, an oleophilic coupler is dissolved in a high-boiling organic solvent, and, then, the resulting solution is directly dispersed in, e.g., a photographic emulsion to made fine colloidal particles, or alternatively, the coupler solution is first dispersed in an aqueous solvent, and then, the resulting solution is added to, e.g., a photographic emulsion.

Dispersion of water-soluble couplers is effected, e.g., in the following manner. As for couplers having one or more ballast groups such as an aliphatic long-chain groups, e.g., an alkyl group or alkylene group with 5 to 20 carbon atoms, and one or more salt-forming groups such as a carboxyl and/or sulfo group, when a hydrophilic water-soluble group is provided to the coupler by converting the coupler into the alkali metal salt thereof, it is feasible to mix the coupler in the form of an aqueous solution with a hydrophilic colloidal composition.

The above coupler is dissolved in a solution of an alkali metal hydroxide in water or in a mixture of water and an alcohol, e.g., ethyl alcohol, e.g., in aqueous sodium hydroxide, alcoholic potassium hydroxide, etc., and then the resulting solution is directly incorporated into a photographic emulsion, or it is incorporated into a hydrophilic colloidal composition such as an aqueous solution of a hydrophilic colloid or a molten gel containing a hydrophilic colloid, which is then added to a photographic emulsion.

Exposure to light for obtaining photographic images can be effected in a conventional in this invention. Any of known various light sources can be used, for example, natural light (sunlight), tungsten lamp, a fluorescent lamp, a xenon arc lamp, a carbon arc lamp, a xenon flash lamp, a cathode ray tube flying spot, etc. The time of exposure can, of course, be 1/1000 sec. to 1 sec. which is usually adopted for cameras, and further, exposure for shorter than 1/1000 sec., for example, $1/10^4$ to $1/10^6$ sec., which is adopted in the case of using a xenon flash lamp or a cathode ray tube, and exposure for longer than 1 sec. can be employed. If necessary, the spectral composition of the light used for exposure can be adjusted by means of a color filter. Lasers can also be used for the exposure.

For the exposure of medical radiation-sensitive materials, an X-ray oscillator and a fluorescent sensitizing screen are generally used. The fluorescent sensitizing screen used for color radiation-sensitive materials is not particularly restricted in this invention, but green light emitting screens as described in U.S. Pat. No. 3,809,906, and Japanese Patent Application Laid-Open (OPI) No. 52,990/74 and No. 63,424/74 are preferably used.

In order to obtain a color image on the color photographic light-sensitive material, development processing is required after exposure. Conventional color development processing basically comprises color development, bleaching (silver-removing) and fixing. Each of the processes may be separately effected, or two or more of the processes may be effected in one treatment by using a processing solution having such functions. A monobath of a bleach-fixing solution is an example thereof. Moreover, each of the processes can be effected two or more times, if desired, or processing comprising a combination of color development, first fixing and bleach-fixing can also be adopted. In addition to the above development processes, various processes such as pre-hardening, neutralizing, first development (black-and-white development), image-stabilizing and washing can be further combined, according to demand. The color radiation-sensitive materials can also be subjected to development processing without a silver-removal step, as described hereinbefore.

The processing temperature is preset within a preferred range depending upon the light-sensitive material and the recipe for the processing. The temperature is, in some cases, less than 18° C, but in most cases, it is 18° C or more. A temperature ranging from 20° to 60° C, and recently, a temperature ranging from 30° to 60° C, is particularly often employed. In particular, color development processing for the color radiation-sensitive materials is preferably effected at 30° to 50° C within 2 minutes, particularly within 1 minute. The preset temperature for a series of processings are not required to be the same as one another, but often such will be the case.

Color developers are alkaline aqueous solutions containing a compound, the oxidized product of which forms a colored product by reacting with a coupler, i.e., a developing agent, and having a pH of 8 or more, preferably 9 to 12.

The above "developing agent" means compounds having a primary amino group on the aromatic ring thereof which are capable of developing exposed silver halide, and precursors which can form such compounds. Preferred typical examples thereof are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfoamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfoamidoethyl-N,N-diethylaniline, and salts thereof (such as the sulfate, hydrochloride, sulfite or p-toluenesulfonate).

Other examples of them are described, e.g., in U.S. Pat. Nos. 2,193,015 and 2,592,364, Japanese Patent Application Laid-Open (OPI) No. 64,933/73, L. F. A. Mason, *Photographic Processing Chemistry*, pp. 226 – 229, Focal Press, London (1966). etc.

In addition, the developing agents are preferably used to together with an auxiliary developing agent such as 3-pyrazolidones.

Various additives can be added to the color developer, if desired. Examples of primary additives are alkali agents such as a hydroxide, carbonate or phosphate of an alkali metal or ammonium; a pH modifier or a buffer, for example, a weak acid such as acetic acid or boric acid, a weak base, salts thereof, etc; a development accelerator, for example, various pyridinium compounds and cationic compounds as described in U.S. Pat. Nos. 2,648,604 and 3,671,247, potassium nitrate sodium nitrate, polyethylene glycol condensates and derivatives thereof as described in U.S. Pat. Nos. 2,533,990; 2,577,127 and 2,950,970, nonionic compounds such as polythioethers represented by the compounds described in British Pat. Nos. 1,020,033 and 1,020,032, polymer compounds having a sulfite ester group as represented by the compounds described in U.S. Pat. No. 3,068,097, as well as organic amines such as pyridine or ethanolamine, benzyl alcohol, hydrazines, etc; and antifogging agent, for example, an alkali metal bromide, an alkali metal iodide, nitrobenzimidazoles as described in U.S. Pat. Nos. 2,496,940 and 2,656,271, mercaptobenzimidazole, 5-methylbenzotriazole, 1-phenyl-5-mercaptotetrazole, compounds for rapid processing solutions as described in U.S. Pat. Nos. 3,113,864; 3,342,596; 3,295,976; 3,615,522 and 3,597,199, thiosulfonyl compounds as described in British Pat. No. 972,211, phenazine-N-oxides as described in Japanese Patent Publication 41,674/71, antifogging agents as described in *Manual of Scientific Photography*, vol. 2, pp. 29 to 47, Maruzen, etc; and anti-stain or anti-sludge agent as described in U.S. Pat. Nos. 3,161,513 and 3,161,514, and British Pat. Nos. 1,030,442; 1,144,481 and 1,251,558; an agent for accelerating the interimage effect as disclosed in U.S. Pat. No. 3,536,487; and a preservative such as a sulfate, hydrogen sulfite, hydroxylamine hydrochloride, a formaldehydebisulfite adduct or an alkanolamine-sulfite adduct. Moreover, couplers can be incorporated into the developer, if desired.

This invention is also applicable to the color intensification method using cobalt complex salts as described in German Patent Application Laid-Open (OLS) Nos. 2,226,770; 2,226,771 and 2,250,050, and the color intensification method using hydrogen peroxide as described in German Patent Applications Laid-Open (OLS) Nos. 1,813,920; 1,950,102; 1,955,901; 1,961,029 and 2,120,091.

Fixing solutions are not particularly restricted in this invention, and those generally used for rapid processing are preferably employed.

In particular, for color radiation-sensitive materials, alkalined fixed solutions (having a pH of 7 or more) are preferably used.

In this invention, automatic processors are preferably used. Any type of the automatic processors, such as (1) a roller conveyor type, (2) a belt conveyor type, (3) a chain conveyor type and (4) a liquid bearing type can be used.

Conventional color light-sensitive materials are, after color development, subjected to bleaching in a conventional manner. This processing may be effected simultaneously with fixing or separately therefrom. If desired, the bleaching solution can be made into a bleach-fixing bath by adding a fixing agent thereto. Many compounds can be used as bleaching agents, but among them, polyvalent metal compounds such as ferricyanates, dichromates, water-soluble cobalt (III) salts, water-soluble copper (II) salts, water-soluble quinones, nitrosophenol, iron (III), cobalt (III) or copper (II), and, particularly, complex salts of these polyvalent metal cations and organic acids, for example, metal complex salts of aminopolycarboxylic acids such as ethylenediaminetetraacetic acid, nitrilotriacetic acid, iminodiacetic acid or N-hydroxyethylethylenediaminetriacetic acid, malonic acid, tartaric acid, glycolic acid or dithioglycolic acid, a copper complex salt of 2,6-dipicolinic acid, etc; peracids such as alkylperacids, persulfates, permanganates or hydrogen peroxide; and hypochlorites such as a hypochlorite, a hypobromite or bleaching powder are generally used alone or as a suitable combination of them.

To the processing solution, various additives including a bleaching accelerator as described in U.S. Pat. Nos. 3,042,520 and 3,241,966, and Japanese Patent Publications Nos. 8,506/70 and 8,836/70 can be further added, if desired.

This invention is further illustrated by the following examples. Unless otherwise indicated, in the following examples all processings were at 40° C and all percentages are weight persentages.

EXAMPLE 1

About 3 g of a coupler having the following structure was dissolved in 50 cc of about a 1 wt% sodium hydroxide aqueous solution at about 40° C.

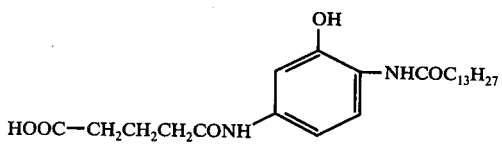

The coupler solution was then added and dispersed in a colloidal solution obtained by adding suitable amounts of citric acid (citric acid: 6 cc of a 10wt% aqueous solution) and chrome alum (chrome alum: 2 cc of a 5wt% aqueous solution) to a gelatin solution containing about 0.04 mol of silver bromoiodide (57g) with an average diameter of 1 to 2 μ (containing 3 mol% of silver iodide). A coating aid (0.5 cc of a 2 wt% aqueous solution of sodium benzenesulfonate) was then added to make a photographic colloidal solution having a pH of 6.5. The colloidal solution was coated on one side of a polyester film 180 microns thick at a silver coverage of 30 mg/100 cm² to prepare a light-sensitive material. The light-sensitive material was exposed to light in an exposure amount of about 0.8 CMS using a sensitometer and then developed at 40° C for 30 seconds with a developer having the following composition, fixed [Hardener-containing acid fixing solution (Trade Name: Fuji-F manufactured by Fuji Photo Film Co., Ltd.); same in the following Examples], washed with water and dried.

| | | |
|---|---|---|
| water | 800 | ml |
| 1-phenyl-3-pyrazolidone | 0.2 | g |
| sodium sulfite | 4.0 | g |
| N,N-diethyl-p-phenylenediamine sulfate | 6.0 | g |
| potassium carbonate | 38.0 | g |
| potassium bromide | 2.0 | g |
| 5-nitrobenzimidazole | 50 | mg |
| compound of this invention | As in Table 1 | |
| water to make | 1000 | ml |

It is evident from the following Table 1 that compounds (18) to (21) of this invention have an effect of accelerating development when added to the above developer.

Table 1

| Compound | Addition Amount (g/l) | Visual Density (Dm) | Fog |
|---|---|---|---|
| control | 0 | 1.70 | 0.23 |
| (18) | 2 | 1.90 | 0.23 |
| (19) | 2 | 1.90 | 0.23 |
| (10) | 2 | 2.10 | 0.24 |
| (20) | 2 | 1.90 | 0.23 |
| (21) | 2 | 1.80 | 0.24 |

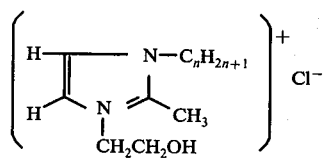

| | |
|---|---|
| Compound (18): in the above formula, | n = 3 |
| Compound (19): " | n = 4 |
| Compound (10): " | n = 6 |
| Compound (20): " | n = 8 |

Table 1-continued

| Compound | Addition Amount (g/l) | Visual Density (Dm) | Fog |
|---|---|---|---|
| Compound (21): | " | | n = 12 |

The "visual density" in the above table refers to the density measured using light which corresponds to the wavelength region of human visual sensitivity.

EXAMPLE 2

The same light-sensitive material as in Example 1 was exposed in an exposure amount of about 0.8 CMS, then developed at 40° C for 30 seconds with a developer having the following composition and fixed, washed with water and dried.

| | | |
|---|---|---|
| water | 800 | ml |
| benzyl alcohol | 10 | ml |
| sodium sulfite | 4.0 | g |
| 4-amino-N-ethyl-N-β-hydroxyethylaniline sulfate | 10 | g |
| potassium carbonate | 30 | g |
| potassium bromide | 2.0 | g |
| 5-nitrobenzimidazole | 30 | mg |
| Compound of the invention | As in Table 2 | |
| water to make | 1000 | ml |

As is evident from the following Table 2, the rate of development can be accelerated by adding compound (10) of this invention to the above developer.

Table 2

| Compound | Addition Amount (g/l) | Visual Density (Dm) | Fog |
|---|---|---|---|
| control | 0 | 1.00 | 0.16 |
| (10) | 2 | 1.30 | 0.17 |

EXAMPLE 3

A cyan coupler, 5-[2-(carboxymethyl)-4-octadecenoylamide]-2-(2-furoylamido)-phenol, which had been dispersed by the oil-soluble type dispersing method was emulsified and mixed with a silver bromoiodide emulsion containing 3 mol% of silver iodide and having an average diameter of 1 to 2 μ, the mixing ratio of the coupler to silver being ¼ mol: 1 mol. Compound 10 of this invention was added as in Table 3. The resulting coating composition was coated on one side of a polyester film 180 μ thick at a silver coverage of about 30 mg per 100 cm² to prepare a light-sensitive material. The light-sensitive material was exposed in an exposure amount of about 0.8 CMS, then developed at 40° C for 30 seconds with the developer of Example 2, fixed, washed with water and dried. As is evident from Table 3, the rate of development can be accelerated by adding compound (10) of this invention to the developer of Example 2.

Table 3

| Compound | Addition Amount (g/l) | Visual Density (Dm) | Fog |
|---|---|---|---|
| control | 0 | 1.20 | 0.16 |
| (10) | 2 | 1.30 | 0.16 |

EXAMPLE 4

A light-sensitive material was prepared in the same manner as in Example 1 except for using a coupler having the following structure.

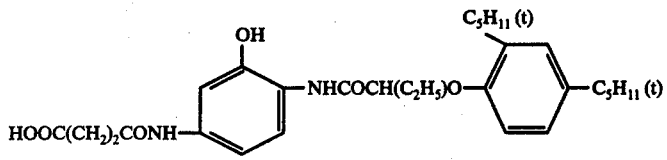

The light-sensitive material was exposed in an exposure amount of about 0.8 CMS, then developed at 40° C for 30 seconds with a developer having the following composition and fixed, washed with water and dried.

| | | |
|---|---|---|
| water | 800 | ml |
| sodium sulfite | 4.0 | g |
| N,N-diethyl-p-phenylenediamine sulfate | 6.0 | g |
| potassium carbonate | 38.0 | g |
| potassium bromide | 2.0 | g |
| 5-nitrobenzimidazole | 30 | mg |
| Compound of this Invention | As in Table 4 | |
| water to make | 1000 | ml |

As is evident from Table 4, the rate of development can be accelerated by adding compound (10) of this invention to the above developer.

Table 4

| Compound | Addition Amount (g/l) | Visual Density (Dm) | Fog |
|---|---|---|---|
| control | 0 | 1.10 | 0.18 |
| (10) | 2 | 1.40 | 0.19 |

EXAMPLE 5

About 3 g of a coupler having the following structure was dissolved in 100 cc of about a 1 wt% sodium hydroxide aqueous solution at about 40° C.

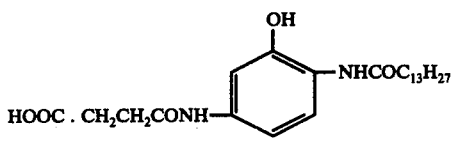

Then, adequate amounts of citric acid and chrome alum were added to a gelatin solution containing about 0.04 mol of silver bromoiodide with an average diameter of 1 to 2 μ (containing 3 mol% of silver iodide) to make a colloidal solution, to which the above coupler solution was then added and dispersed therein. To 100 g of the resulting emulsion, 4 ml of a 16 % aqueous solution of compound (10) of this invention was added, and, further, sodium dodecylbenzenesulfonate was added as a coating aid, thus preparing a photographic colloidal solution having a pH of about 6.5. The colloidal solution was coated on one side of a polyester film 180 microns thick so as to provide a film thickness of about 10 μ (dry basis), thus making a sample of a photographic light-sensitive material. The sample was exposed in an exposure amount of about 0.8 CMS using a sensitometer, and then processed as in Example 1. The results obtained are shown in Table 5.

Table 5

| Compound | Visual Density (Dm) | Fog |
|---|---|---|
| control | 1.70 | 0.23 |
| (10) | 2.10 | 0.24 |

By the addition of the compound of this invention, maximum density increased and fog was less increased

EXAMPLE 6

A commercially available motion-picture positive film comprising a fine-grain silver chlorobromoiodide gelatin emulsion (Fuji Fine-Grain Positive Film made by Fuji Photo Film Co., Ltd.) was exposed (4800° K, 500 lux, 1 sec.) and developed at 20° C for 4 to 8 min. with a developer having the following composition, whereafter stopping was conducted for 30 seconds, fixing for 3 minutes and washing for 5 minutes (all at 20° C), stopping being with a 3% aqueous solution of glacial acetic acid and fixing being with Kodak F-5.

| | | |
|---|---|---|
| water | 800 | ml |
| N-methyl-p-aminophenol sulfate | 1.7 | g |
| sodium sulfite | 50 | g |
| hydroquinone | 4.4 | g |
| borax | 10 | g |
| potassium bromide | 0.5 | g |
| Compound of this Invention | As in Table 6 | |
| Water to make | 1 liter | |

Development by the above developer usually takes 8 minutes.

As is evident from Table 6, the time of development can be decreased by adding compound (10) of this invention to the developer. Moreover, when the compound of this invention is added, and development is likewise effected for 8 minutes, processing can be effected to obtain a higher sensitivity, as is seen from Table 6. For comparison, photographic characteristic values obtained by adding a quaternary salt compound (A), known in the art, are also shown.

Table 6

| Compound | Addition Amount (g/l) | Development Time of 8 min. | | | Time required to obtain a relative sensitivity of 100 |
|---|---|---|---|---|---|
| | | Relative Sensitivity | Fog | Gamma | |
| control | 0 | 100 | 0.04 | 1.70 | 8 min. |
| (10) | 2 | 200 | 0.05 | 2.18 | 4 min. |
| (A) | 2 | 160 | 0.12 | 2.02 | 5 min. |

Comparative Compound (A)

$$\langle\phantom{X}\rangle - N^+ - (CH_2)_3 - N^+ - \langle\phantom{X}\rangle \cdot 2Cl^-$$

The comparative compound provided a large increase in fog.

The use of the compound of this invention resulted in a very small increase in fog and a remarkable increase in sensitivity.

Example 7

A micro film (Mini Copy Film HR, made by Fuji Photo Film Co., Ltd.) comprising a fine-grain silver chlorobromoiodide gelatin emulsion coated on a support was exposed (2854° K, 1250 lux, 1/25 sec.) and developed at 20° C using the following developer. The processing conditions were otherwise the same as in Example 6, except for the fact that the development time was 2 to 4 minutes.

| | | |
|---|---|---|
| water | 800 | ml |
| N-methyl-p-aminophenol sulfate | 1.0 | g |
| sodium sulfite | 75 | g |
| hydroquinone | 9.0 | g |
| sodium carbonate monohydrate | 29 | g |
| potassium bromide | 6.0 | g |
| Compound of this Invention | As in Table 7 | |
| water to make | 1 liter | |

Development by this developer usually takes 4 minutes. However, the time of development could be decreased by adding compound (10) or (15) of this invention to the developer, as is seen from Table 7. Moreover, when the compound of this invention was added, and the development was likewise effected for 4 minutes, processing could be effected to obtain a higher sensitivity, as is seen from Table 7.

Table 7

| Compound | Addition Amount (mol/l) | Development Time of 4 min. Relative Sensitivity | Fog | Gamma | Time required to obtain a relative sensitivity of 100 |
|---|---|---|---|---|---|
| control | 0 | 100 | 0.19 | 4.00 | 4 min. |
| (10) | $1 \times 10^{-2}$ | 145 | 0.20 | 4.15 | 2 min. |
| (15) | $1 \times 10^{-2}$ | 140 | 0.21 | 4.08 | 2 min. and 30 sec. |

EXAMPLE 8

An aqueous solution of compound (10) or (16) of this invention was added to a silver bromoiodide gelatin emulsion containing 3.0 mol% silver iodide, which was then coated on a film base and dried. The sample film was developed at 20° C for 8 minutes using the developer of Example 6. The processing conditions were otherwise the same as in Example 6, except for the fact that the development time was 8 minutes. The photographic characteristic values obtained are shown in Table 8.

Table 8

| Compound | Addition Amount (g/mol of silver halide) | Characteristic Value Relative Sensitivity | Fog | Gamma |
|---|---|---|---|---|
| control | 0 | 100 | 0.07 | 0.82 |
| (10) | 1 | 145 | 0.09 | 0.86 |
| (16) | 1 | 140 | 0.10 | 0.90 |

EXAMPLE 9

1-hydroxy-4-chloro-2-n-dodecylnaphthamide (a cyan coupler) was emulsified and mixed in a red-sensitive silver bromoiodide emulsion (containing 7 mol% of silver iodide). 1-(2',4',6'-trichlorophenyl)-3-[3'''-(2''',4'''-di-t-amylphenoxyacetamido)-benzamido]-5-pyrazolone (as a magenta coupler) was emulsified and mixed in a green-sensitive silver bromoiodide emulsion (containing 6 mol% of silver iodide). α-(2-methylbenzoyl)-aceto-(2'-chloro-5'-dodecoxycarbonyl)anilide (a yellow coupler) was emulsified and mixed in a blue-sensitive silver bromoiodide emulsion (containing 6 mol% of silver iodide). A color negative photographic light-sensitive material was prepared by coating the above emulsions on a triacetate film base and then subjected to the following test.

In the above emulsification of each coupler, dibutyl phthalate and tricresyl phosphate were used as solvents for the couplers, sorbitan monolaurate and sodium dodecylbenzenesulfonate were used as emulsifiers, and sodium 1-(p-nonylphenoxytrioxyethylene)-butane-4-sulfonate and the lauric ester of sucrose were added as coating aids.

This film was exposed to light (4800° K, 2500 lux, 1/50 sec.) and then treated as follows.

| Treatment Processes | | | |
|---|---|---|---|
| Color Development | 38° C | 3¼ | min. |
| Bleaching Bath | " | 6½ | min. |
| Washing | " | 3¼ | min. |
| Fixing Bath | " | 6½ | min. |
| Washing | " | 3¼ | min. |
| Stabilizing | " | 1½ | min. |
| Drying | " | | |

| Color Developer | | |
|---|---|---|
| sodium sulfite | 2.0 | g |
| sodium carbonate (monohydrate) | 30 | g |
| potassium bromide | 2.0 | g |
| hydroxylamine sulfate | 3.0 | g |
| 3-methyl-4-amino-N-ethyl-N-β-hydroxyethylaniline sulfate | 5.0 | g |
| water to make | 1 liter | |

| Bleaching Solution | | |
|---|---|---|
| ammonium bromide | 150 | g |
| aqueous ammonia (28%) | 5 | ml |
| iron (III) salt of sodium ethylenediaminetetraacetate | 100 | g |
| Water to make | 1 liter | |

| Fixing Solution | | |
|---|---|---|
| sodium tetrapolyphosphate | 2.0 | g |
| sodium sulfite | 15 | g |
| ammonium thiosulfate (70% solution) | 150 | ml |
| water to make | 1 liter | |

| Stabilizing Solution | | |
|---|---|---|
| formaldehyde (37% solution) | 4 | cc |

-continued

| Stabilizing Solution | |
|---|---|
| water to make | 1 liter |

As is evident from the following Table 9, the processing could be effected to obtain higher sensitivity by adding compound (10) of this invention to the color developer.

Table 9

| Compound | Addition Amount (g/l) | Fog | | | Relative Sensitivity | | |
|---|---|---|---|---|---|---|---|
| | | Red | Green | Blue | Red | Green | Blue |
| control | 0 | 0.08 | 0.10 | 0.12 | 100 | 100 | 100 |
| (10) | 1 | 0.08 | 0.11 | 0.14 | 120 | 125 | 130 |

While the invention has been described in detail and with reference to specific embodiments thereof, it will be apparent to one skilled in the art that various changes and modifications can be made therein without departing from the spirit and scope thereof.

What is claimed is:

1. A method of developing a silver halide photographic light-sensitive material which comprises imagewise exposing said material to light, developing the photographic light-sensitive material with a silver halide developing agent in the presence of a compound selected from the group consisting of

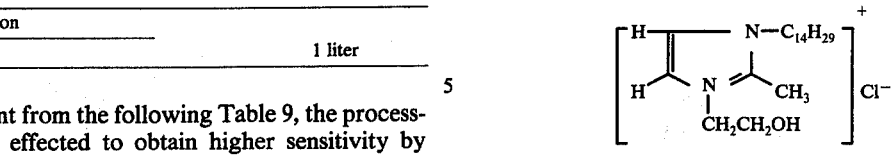

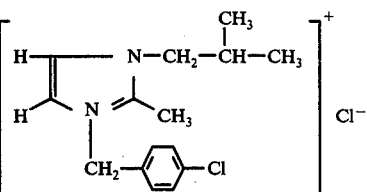

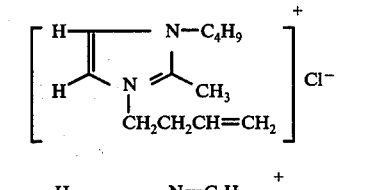

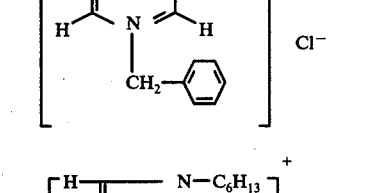

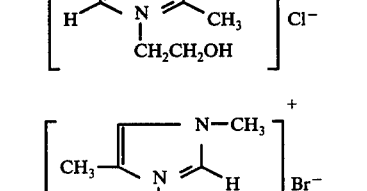

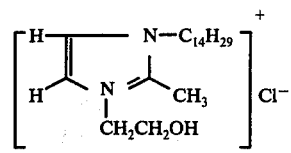

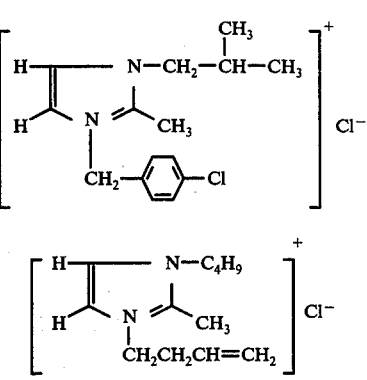

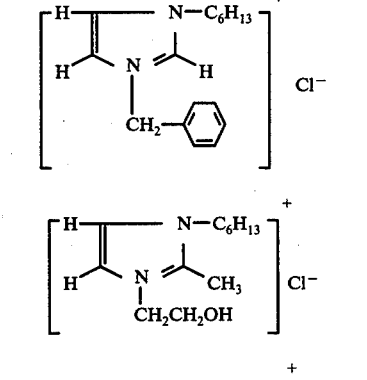

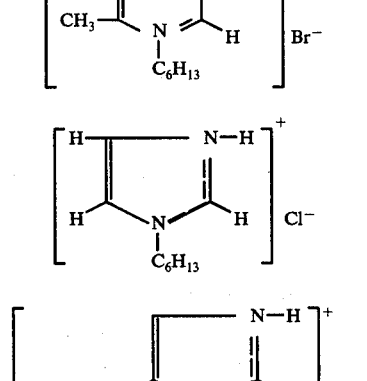

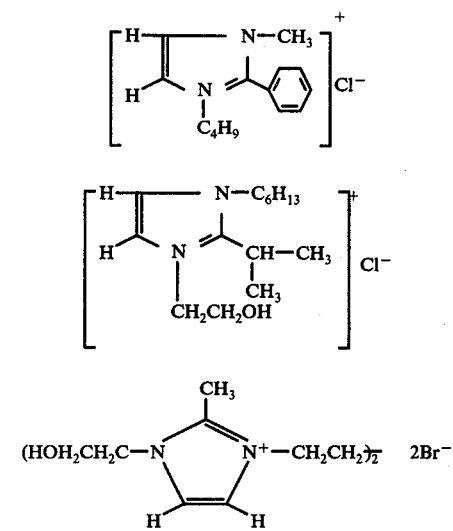

said compound being present in a bath prior to development, the developer bath, or a silver halide emulsion layer of the photographic light-sensitive material.

2. The method of claim 1, wherein said processing bath is the developer.

3. The method of claim 2, wherein the amount of said one or more compounds is from about 0.01 g to about 100 g per 1 liter of the developer.

4. The method of claim 1, wherein said one or more compounds are added to the silver halide photographic light-sensitive material.

5. The method of claim 4, wherein the amount of said one or more compounds added is about 0.01 g to 50 g per 1 mol of silver halide.

6. The method of claim 1, wherein said compound is

7. The method of claim 1, wherein said compound is

8. The method of claim 1, wherein said compound is

9. The method of claim 1, wherein said compound is

10. The method of claim 1, wherein said compound is

11. The method of claim 1, wherein said compound is

12. The method of claim 1, wherein said compound is

13. The method of claim 1, wherein said compound is

14. The method of claim 1, wherein said compound is

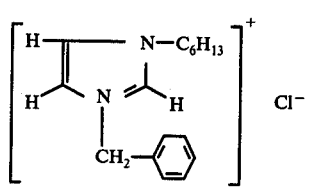
15. The method of claim 1, wherein said compound is
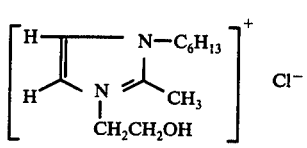
16. The method of claim 1, wherein said compound is
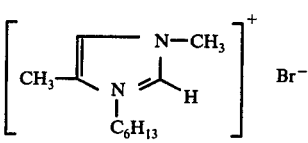
17. The method of claim 1, wherein said compound is
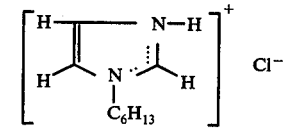
18. The method of claim 1, wherein said compound is
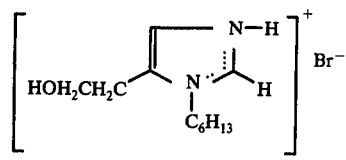
19. The method of claim 1, wherein said compound is
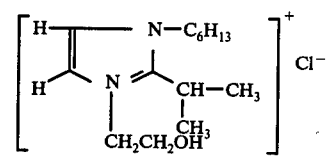
20. The method of claim 1, wherein said compound is
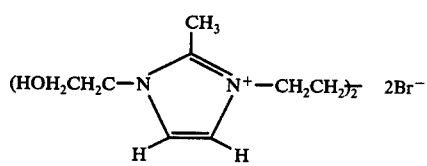
21. The method of claim 1, wherein said compound is
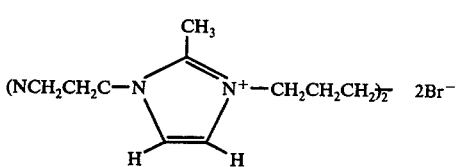
22. The method of claim 1, wherein said compound is
* * * * *